United States Patent [19]
Dudar et al.

[11] Patent Number: 5,776,125
[45] Date of Patent: Jul. 7, 1998

[54] NEEDLELESS VIAL ACCESS DEVICE

[75] Inventors: Thomas E. Dudar, Palatine, Ill.; Peter L. Graham, Pinckney, Mich.; Steven C. Jepson, Palatine, Ill.

[73] Assignee: Baxter International Inc., Deerfield, Ill.

[21] Appl. No.: 427,063

[22] Filed: Apr. 24, 1995

Related U.S. Application Data

[63] Continuation-in-part of Ser. No. 737,735, Jul. 30, 1991, Pat. No. 5,411,499.

[51] Int. Cl.[6] ............................................. A61M 37/00
[52] U.S. Cl. .................................. 606/411; 604/88
[58] Field of Search .................. 606/87, 88, 200–206, 606/166, 283, 411–415; 215/247; 604/164

[56] References Cited

U.S. PATENT DOCUMENTS

| | | |
|---|---|---|
| 1,180,665 | 4/1916 | McElroy . |
| 2,102,704 | 12/1937 | Hein . |
| 2,183,900 | 12/1939 | Voit et al. . |
| 2,325,929 | 8/1943 | Amesbury et al. . |
| 2,436,291 | 12/1948 | Daniel . |
| 2,546,672 | 3/1951 | LeClair . |
| 2,577,780 | 12/1951 | Lockhart . |
| 2,579,724 | 12/1951 | Breakstone . |
| 2,579,725 | 12/1951 | Breakstone . |
| 2,908,274 | 10/1959 | Bujan . |
| 2,912,980 | 11/1959 | Beachum et al. . |
| 2,989,053 | 6/1961 | Hamilton . |
| 2,998,635 | 9/1961 | Burritt, Jr. et al. . |
| 3,057,350 | 10/1962 | Cowley . |
| 3,064,652 | 11/1962 | Corcoran et al. . |
| 3,233,727 | 2/1966 | Wilson . |
| 3,245,698 | 4/1966 | Fromknecht . |
| 3,313,299 | 4/1967 | Spademan . |
| 3,332,418 | 7/1967 | Brody . |
| 3,376,866 | 4/1968 | Ogle . |

(List continued on next page.)

FOREIGN PATENT DOCUMENTS

| | | |
|---|---|---|
| 13945 | 10/1971 | Australia . |
| 964544 | 3/1975 | Canada . |
| 1043744 | 12/1978 | Canada . |
| 1215945 | 12/1986 | Canada . |
| 0021405 | 1/1981 | European Pat. Off. . |
| 0050459 | 4/1982 | European Pat. Off. . |
| 0109903 | 5/1984 | European Pat. Off. . |
| 0111723 | 6/1984 | European Pat. Off. . |
| 0114677 | 8/1984 | European Pat. Off. . |
| 0116986 | 8/1984 | European Pat. Off. . |
| 0127781 | 12/1984 | European Pat. Off. . |
| 0157224 | 10/1985 | European Pat. Off. . |
| 0169704 | 1/1986 | European Pat. Off. . |

(List continued on next page.)

OTHER PUBLICATIONS

Industrie BORLA S.p.A. General Catalog, 1980 p. 1, PF0084.
Industrie BORLA S.p.A. Catalogs, Each of 1981–1992 (Any of PF0084, PF0091, PF0358, PF0241, PF0392, PF0218).
Components for I.V. infusion and blood transfusion sets (patient-side terminals) Undated (1980–1986); pp. PF0358, PF0241, PF0392, PF0218.
Travenol Nutrition Products, 1982 pp. BX 77331, 77533–77534.
Schematic Drawing of Automix (Undated), p. BX 77314.
Section 5—Operation (Undated), pp. 5–2 through 5–14 BX77315–77328.
Travenol CYSTOFLO™ advertising literature (Undated) pp. BX 77333–77334.

(List continued on next page.)

Primary Examiner—William Lewis
Attorney, Agent, or Firm—Jeffrey C. Nichols; Mark J. Buonaiuto; Frances J. Kowalik

[57] ABSTRACT

The present invention provides a piercing member adapted for use with a flow channel. The piercing member has a penetrating member for piercing a solid closure, and is retained to the flow channel, but still allows fluid to flow through the flow channel while retained to the flow channel.

30 Claims, 11 Drawing Sheets

U.S. PATENT DOCUMENTS

| | | |
|---|---|---|
| 3,394,954 | 7/1968 | Sarns . |
| 3,447,570 | 6/1969 | Collins . |
| 3,478,743 | 11/1969 | Ericson . |
| 3,577,992 | 5/1971 | Merry et al. . |
| 3,593,909 | 7/1971 | Bergmann . |
| 3,598,124 | 8/1971 | Andersen . |
| 3,602,009 | 8/1971 | Powell . |
| 3,604,420 | 9/1971 | Vaillancourt . |
| 3,695,478 | 10/1972 | Sie et al. . |
| 3,729,031 | 4/1973 | Baldwin . |
| 3,729,032 | 4/1973 | Tischlinger . |
| 3,741,217 | 6/1973 | Ciarico . |
| 3,746,001 | 7/1973 | Ralston, Jr. . |
| 3,768,473 | 10/1973 | Shields . |
| 3,770,155 | 11/1973 | Novitch . |
| 3,776,229 | 12/1973 | McPhee . |
| 3,823,840 | 7/1974 | Zackheim . |
| 3,826,260 | 7/1974 | Killinger . |
| 3,837,381 | 9/1974 | Arroyo . |
| 3,848,593 | 11/1974 | Baldwin . |
| 3,851,647 | 12/1974 | Monestere, Jr. et al. . |
| 3,853,127 | 12/1974 | Spademan . |
| 3,900,028 | 8/1975 | McPhere . |
| 3,904,059 | 9/1975 | Belolamy, Jr. et al. . |
| 3,976,073 | 8/1976 | Quick et al. . |
| 3,977,400 | 8/1976 | Moorehead . |
| 3,986,508 | 10/1976 | Barrington . |
| 3,990,445 | 11/1976 | Lundquist . |
| 3,994,293 | 11/1976 | Ferro . |
| 3,995,630 | 12/1976 | Van de Veerdonk . |
| 4,000,739 | 1/1977 | Stevens . |
| 4,000,740 | 1/1977 | Mittleman . |
| 4,048,995 | 9/1977 | Mittleman . |
| 4,048,996 | 9/1977 | Mittleman . |
| 4,066,556 | 1/1978 | Vaillancourt . |
| 4,123,081 | 10/1978 | Consentino et al. . |
| 4,127,131 | 11/1978 | Vaillancourt . |
| 4,130,932 | 12/1978 | Epmeier . |
| 4,133,441 | 1/1979 | Mittleman . |
| 4,134,512 | 1/1979 | Nugent . |
| 4,143,853 | 3/1979 | Abramson . |
| 4,153,057 | 5/1979 | Köbel . |
| 4,177,814 | 12/1979 | Knepshield et al. . |
| 4,197,848 | 4/1980 | Garrett et al. . |
| 4,205,675 | 6/1980 | Vaillancourt . |
| 4,219,912 | 9/1980 | Adams . |
| 4,232,669 | 11/1980 | Nitshke . |
| 4,236,880 | 12/1980 | Archibald . |
| 4,243,034 | 1/1981 | Brandt . |
| 4,243,150 | 1/1981 | Gunne . |
| 4,244,364 | 1/1981 | Grushkin . |
| 4,246,899 | 1/1981 | Loseff . |
| 4,259,276 | 3/1981 | Rawlings . |
| 4,276,170 | 6/1981 | Vaillancourt . |
| 4,277,226 | 7/1981 | Archibald . |
| 4,289,129 | 9/1981 | Turner . |
| 4,294,249 | 10/1981 | Sheehan et al. . |
| 4,303,067 | 12/1981 | Connolly et al. . |
| 4,311,137 | 1/1982 | Gerard . |
| 4,322,201 | 3/1982 | Archibald . |
| 4,326,569 | 4/1982 | Vaillancourt . |
| 4,328,802 | 5/1982 | Curley et al. . |
| 4,331,254 | 5/1982 | Haggerty . |
| 4,334,551 | 6/1982 | Pfister . |
| 4,360,024 | 11/1982 | Wallace . |
| 4,362,156 | 12/1982 | Feller et al. . |
| 4,372,100 | 2/1983 | Miller et al. . |
| 4,387,879 | 6/1983 | Tauschinski . |
| 4,405,316 | 9/1983 | Mittleman . |
| 4,405,320 | 9/1993 | Cracaver et al. . |
| 4,410,321 | 10/1983 | Pearson et al. . |
| 4,411,661 | 10/1983 | Kersten . |
| 4,411,662 | 10/1983 | Pearson . |
| 4,412,573 | 11/1983 | Zdeb . |
| 4,416,661 | 11/1983 | Norman et al. . |
| 4,417,888 | 11/1983 | Consentino et al. . |
| 4,424,833 | 1/1984 | Spector et al. . |
| 4,430,081 | 2/1984 | Timmermans . |
| 4,434,822 | 3/1984 | Bellamy et al. . |
| 4,436,519 | 3/1984 | O'Neill . |
| 4,439,188 | 3/1984 | Dennehey et al. . |
| 4,445,896 | 5/1984 | Gianturco . |
| 4,475,548 | 10/1984 | Muto . |
| 4,496,348 | 1/1985 | Genese et al. . |
| 4,511,359 | 4/1985 | Vaillancourt . |
| 4,535,820 | 8/1985 | Raines . |
| 4,545,367 | 10/1985 | Tucci . |
| 4,559,043 | 12/1985 | Whitehouse et al. . |
| 4,578,063 | 3/1986 | Inman et al. . |
| 4,588,403 | 5/1986 | Weiss et al. . |
| 4,589,879 | 5/1986 | Pearson . |
| 4,601,703 | 7/1986 | Herlitze . |
| 4,607,671 | 8/1986 | Aalto et al. . |
| 4,610,374 | 9/1986 | Buehler . |
| 4,610,469 | 9/1986 | Wolff-Mooij . |
| 4,610,665 | 9/1986 | Matsumoto et al. . |
| 4,610,674 | 9/1986 | Suzuki et al. . |
| 4,617,012 | 10/1986 | Vaillancourt . |
| 4,624,393 | 11/1986 | Lopez . |
| 4,624,667 | 11/1986 | Rutnarak . |
| 4,626,245 | 12/1986 | Weinstein . |
| 4,634,424 | 1/1987 | O'Boyle . |
| 4,637,817 | 1/1987 | Archibald et al. . |
| 4,638,809 | 1/1987 | Kuperus . |
| 4,645,495 | 2/1987 | Vaillancourt . |
| 4,650,475 | 3/1987 | Smith et al. . |
| 4,653,010 | 3/1987 | Figler et al. . |
| 4,655,750 | 4/1987 | Vaillancourt . |
| 4,655,752 | 4/1987 | Honkanen et al. . |
| 4,662,878 | 5/1987 | Lindmayer . |
| 4,673,386 | 6/1987 | Gordon . |
| 4,673,390 | 6/1987 | Archibald . |
| 4,673,393 | 6/1987 | Suzuki et al. . |
| 4,675,020 | 6/1987 | McPhee . |
| 4,683,916 | 8/1987 | Raines . |
| 4,704,177 | 11/1987 | Vaillancourt . |
| 4,705,506 | 11/1987 | Archibald . |
| 4,711,636 | 12/1987 | Bierman . |
| 4,714,463 | 12/1987 | Archibald . |
| 4,718,467 | 1/1988 | DiGianfilippo et al. . |
| 4,723,550 | 2/1988 | Bales et al. . |
| 4,735,311 | 4/1988 | Lowe et al. . |
| 4,745,950 | 5/1988 | Mathieu . |
| 4,752,292 | 6/1988 | Lopez et al. . |
| 4,758,225 | 7/1988 | Cox et al. . |
| 4,759,756 | 7/1988 | Forman et al. . |
| 4,760,847 | 8/1988 | Vaillancourt . |
| 4,763,648 | 8/1988 | Wyatt . |
| 4,765,588 | 8/1988 | Atkinson . |
| 4,766,843 | 8/1988 | Murakami et al. . |
| 4,768,568 | 9/1988 | Fournier et al. . |
| 4,770,295 | 9/1988 | Carveth et al. . |
| 4,776,843 | 10/1988 | Martinez et al. . |
| 4,781,680 | 11/1988 | Redmond et al. . |
| 4,789,014 | 12/1988 | DiGianfilippo et al. . |
| 4,796,615 | 1/1989 | Bullock et al. . |
| 4,798,594 | 1/1989 | Hillstead . |
| 4,804,366 | 2/1989 | Zdeb et al. . |
| 4,809,679 | 3/1989 | Shimonaka et al. . |
| 4,810,241 | 3/1989 | Rogers . |
| 4,813,937 | 3/1989 | Vaillancourt . |
| 4,822,343 | 4/1989 | Biser . |

| | | | | | | |
|---|---|---|---|---|---|---|
| 4,823,833 | 4/1989 | Hogan et al. . | | 0324839 | 8/1991 | European Pat. Off. . |
| 4,834,152 | 5/1989 | Howson et al. . | | 0471335 | 2/1992 | European Pat. Off. . |
| 4,834,709 | 5/1989 | Banning et al. . | | 0485028 | 5/1992 | European Pat. Off. . |
| 4,834,716 | 5/1989 | Ogel, II . | | 0495330 | 7/1992 | European Pat. Off. . |
| 4,838,855 | 6/1989 | Lynn . | | 0563617 | 10/1993 | European Pat. Off. . |
| 4,840,017 | 6/1989 | Miller et al. . | | 1171578 | 1/1902 | France . |
| 4,842,591 | 6/1989 | Luther . | | 1171578 | 1/1959 | France . |
| 4,850,978 | 7/1989 | Dudar et al. . | | 1373027 | 4/1964 | France . |
| 4,857,062 | 8/1989 | Russell . | | 2439022 | 6/1980 | France . |
| 4,874,369 | 10/1989 | Kulle et al. . | | 2539303 | 7/1984 | France . |
| 4,874,377 | 10/1989 | Newgard et al. . | | 35387 | 11/1965 | German Dem. Rep. . |
| 4,874,378 | 10/1989 | Hillstead . | | 0855319 | 11/1952 | Germany . |
| 4,878,516 | 11/1989 | Mathieu . | | GM7443346 | 10/1977 | Germany . |
| 4,886,495 | 12/1989 | Reynolds . | | TI441387 | 11/1978 | Germany . |
| 4,889,256 | 12/1989 | Fowies . | | 3303718 | 10/1984 | Germany . |
| 4,892,222 | 1/1990 | Schmidt et al. . | | 8425197 | 10/1985 | Germany . |
| 4,895,346 | 1/1990 | Steigerwald . | | 3627978 | 8/1986 | Germany . |
| 4,895,565 | 1/1990 | Hillstead . | | 548632 | 9/1956 | Italy . |
| 4,909,794 | 3/1990 | Haber et al. . | | 50-9195 | 3/1975 | Japan . |
| 4,909,798 | 3/1990 | Fleischhacker et al. . | | 55-1628 | 1/1980 | Japan . |
| 4,911,705 | 3/1990 | Heinzerling et al. . | | 56-501668 | 11/1981 | Japan . |
| 4,915,687 | 4/1990 | Sivert . | | 62-43697 | 9/1987 | Japan . |
| 4,915,690 | 4/1990 | Cone et al. . | | 3-504571 | 10/1991 | Japan . |
| 4,932,633 | 6/1990 | Johnson et al. . | | 1898158 | 1/1995 | Japan . |
| 4,932,944 | 6/1990 | Jagger et al. . | | 361364 | 5/1962 | Switzerland . |
| 4,935,010 | 6/1990 | Cox et al. . | | 1625650 | 2/1991 | U.S.S.R. . |
| 4,936,832 | 6/1990 | Vaillancourt . | | 843744 | 8/1960 | United Kingdom . |
| 4,946,445 | 8/1990 | Lynn . | | 893754 | 4/1962 | United Kingdom . |
| 4,950,260 | 8/1990 | Bonaldo . | | 927020 | 5/1963 | United Kingdom . |
| 4,961,729 | 10/1990 | Vaillancourt . | | 1078650 | 8/1967 | United Kingdom . |
| 4,966,586 | 10/1990 | Vaillancourt . | | 2033230 | 5/1980 | United Kingdom . |
| 4,967,811 | 11/1990 | DiGianfilippo et al. . | | 2067075 | 11/1983 | United Kingdom . |
| 4,981,469 | 1/1991 | Whitehouse et al. . | | 2143134 | 2/1985 | United Kingdom . |
| 4,994,029 | 2/1991 | Rohrbough . | | WO 89/06553 | 7/1989 | WIPO . |
| 4,998,713 | 3/1991 | Vaillancourt . | | WO 90/12606 | 1/1990 | WIPO . |
| 5,009,391 | 4/1991 | Steigerwald . | | WO 90/11103 | 10/1990 | WIPO . |
| 5,009,640 | 4/1991 | Pyret et al. . | | WO 91/05581 | 5/1991 | WIPO . |
| 5,017,192 | 5/1991 | Dodge et al. . | | WO 91/07206 | 5/1991 | WIPO . |
| 5,035,014 | 7/1991 | Van Heugtien . | | WO 91/10459 | 7/1991 | WIPO . |
| 5,053,014 | 10/1991 | Van Heugten . | | WO 92/04936 | 4/1992 | WIPO . |
| 5,059,172 | 10/1991 | Sutherland et al. . | | | | |
| 5,059,186 | 10/1991 | Yamamoto et al. . | | | | |
| 5,071,404 | 12/1991 | Larkin et al. . | | | | |
| 5,071,413 | 12/1991 | Utterberg . | | | | |
| 5,078,689 | 1/1992 | Keller . | | | | |
| 5,080,654 | 1/1992 | Picha et al. . | | | | |
| 5,088,995 | 2/1992 | Packard et al. . | | | | |
| 5,100,394 | 3/1992 | Dudar et al. . | | | | |
| 5,135,489 | 8/1992 | Jepson et al. . | | | | |
| 5,149,327 | 9/1992 | Oshiyama . | | | | |
| 5,178,607 | 1/1993 | Lynn et al. . | | | | |
| 5,188,620 | 2/1993 | Jepson et al. . | | | | |
| 5,199,947 | 4/1993 | Lopez et al. . | | | | |
| 5,211,638 | 5/1993 | Dudar et al. . | | | | |
| 5,447,495 | 9/1995 | Lynn et al. . | | | | |

FOREIGN PATENT DOCUMENTS

| | | |
|---|---|---|
| 0220911 | 5/1987 | European Pat. Off. . |
| 0232074 | 8/1987 | European Pat. Off. . |
| 0143517 | 5/1989 | European Pat. Off. . |
| 0319764 | 6/1989 | European Pat. Off. . |
| 0344907 | 12/1989 | European Pat. Off. . |
| 0367549 | 5/1990 | European Pat. Off. . |
| 0395758 | 11/1990 | European Pat. Off. . |
| 0413386 | 2/1991 | European Pat. Off. . |

OTHER PUBLICATIONS

Compounding Perspectives: A Newsletter for Users of AUTOMIX™ & AUTOMIX™ PLUS Compounders Fall 1986 pp. BX 77297–77300.

Clintec Nutrition Travesorb® Dual Port Feeding Tubes, (Undated) pp. BX 77536–77539.

Travenol Laboratories Parenteral Products Division Catalog, 1982–Photograph.

"I.V. Sets and Solutions Safeline No–Needle I.V. System", article by Kendall McGaw Laboratories, Inc. (Undated).

1991 Annual Report of Becton Dickinson, 1991.

"Needlestick–Prevention Devices", Special Report and Product Review, Health Devices, May 1991, vol. 20, No. 5, pp. 154–181.

IMED Needleless System, 1993.

Ped–Pod Oral Dispenser and Hy–Pod Hypodermic Syringes, SoloPack Laboratories, Elk Grove Village, IL (Undated).

European Application 84 100 561.4, to Lopez, Jan. 19, 1984 (filing date), 1–4 and Declaration of Dr. Lopez.

Burron's SafSite . . . remove the risk; (Undated); pp. M44956–44959.

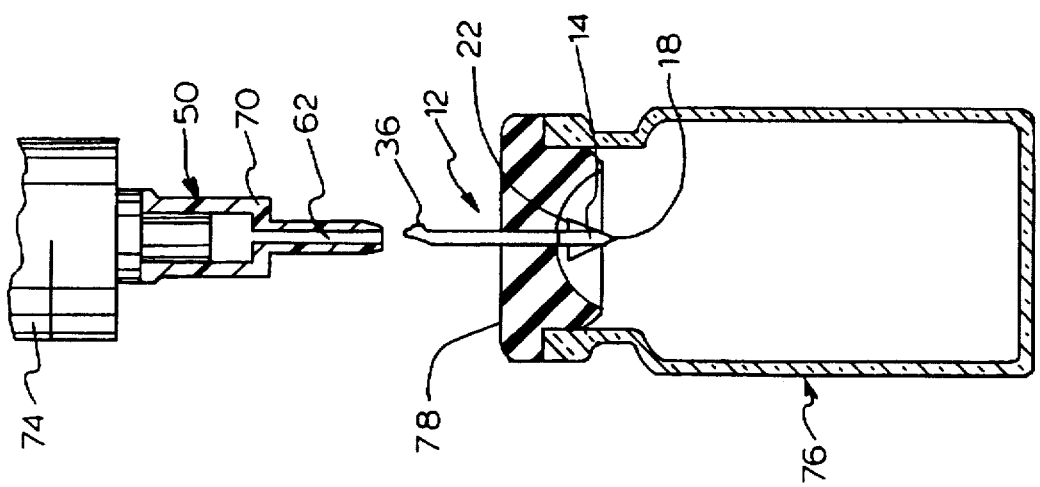
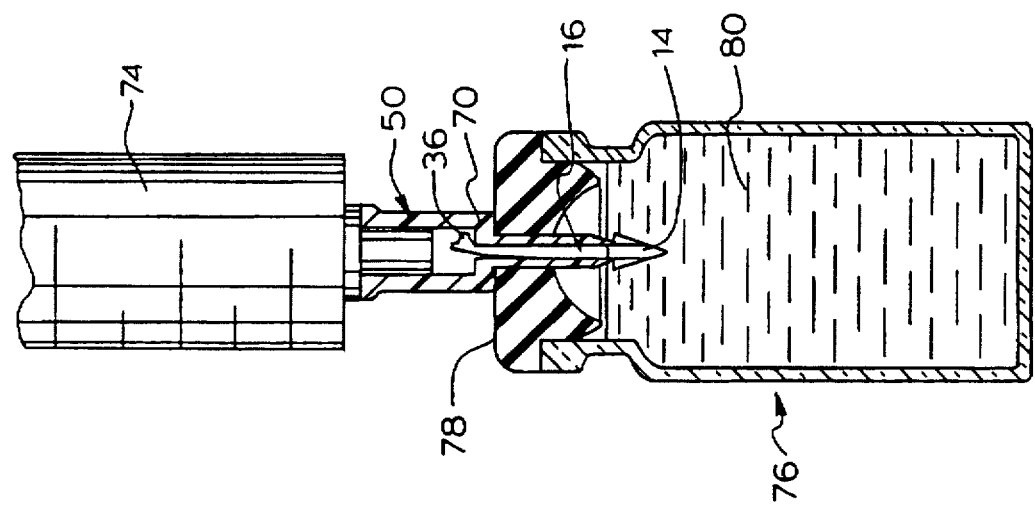
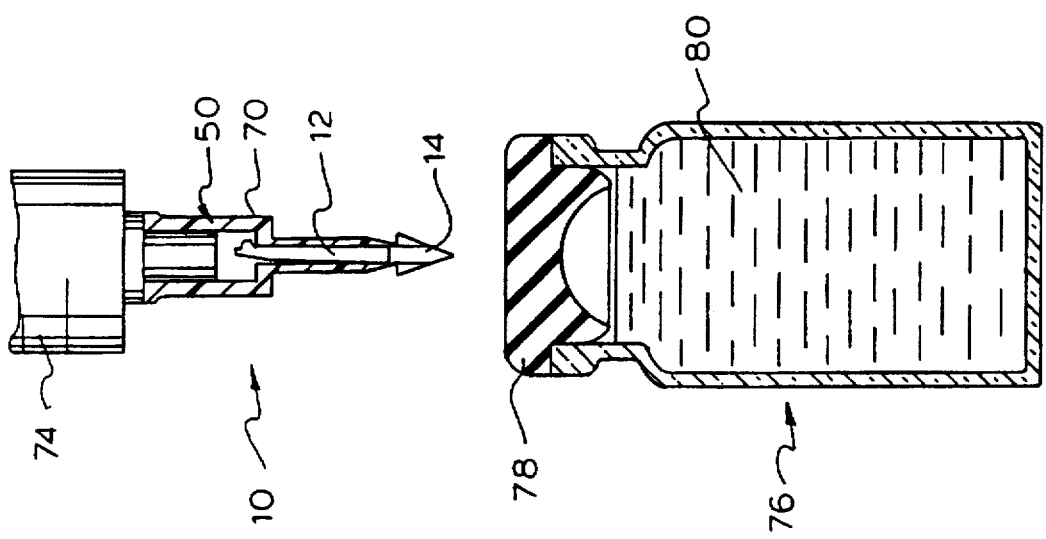

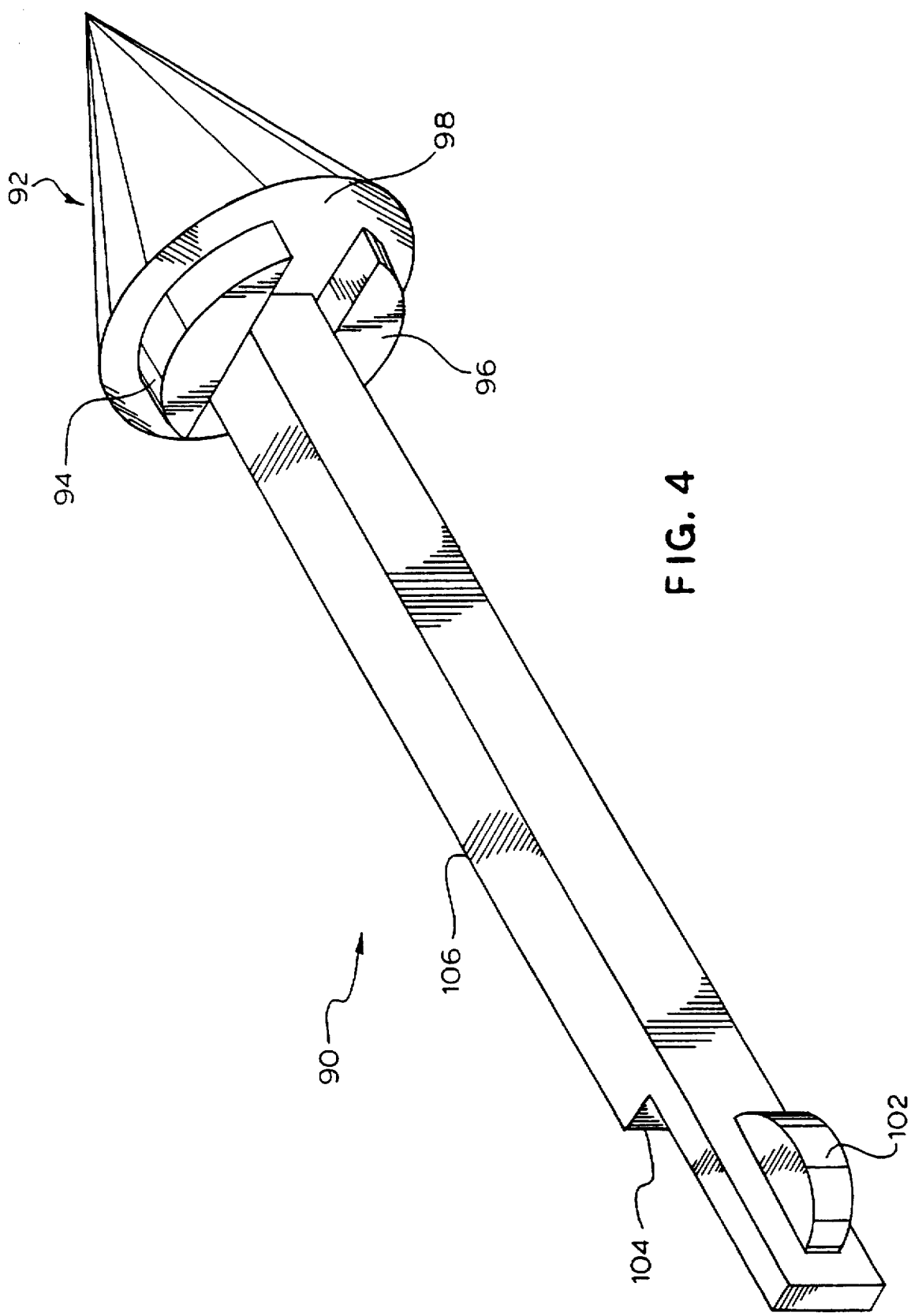

NEEDLELESS VIAL ACCESS DEVICE

RELATED APPLICATION

This application is a continuation-in-part application of the commonly assigned U.S. patent application Ser. No. 07/737,735, filed on Jul. 30, 1991 now U.S. Pat. No. 5,411,499.

DESCRIPTION

1. Field of the Invention

The invention generally pertains to medical products and more particularly to a blunt cannula assembly having a piercing tip associated therewith to penetrate a rubber septum of a drug access vial to access the vial contents with the blunt cannula.

2. Background of the Invention

In the medical field, it is common to access the vascular system of a patient by inserting a venous catheter into a patient's vein. The catheter may be connected through tubing to I.V. solution containers or other fluid sources. It is also customary to provide injection sites along the tubing flow path for the administration of supplemental fluids for treatment of the patient.

Injection sites usually have a housing defining a fluid flow path which is connected at one end to the tubing to the patient and closed at an opposite end by an elastomeric or rubber septum. The septum prevents contaminants from making their way into the vascular system of the patient. A pointed cannula or needle can be forced through the septum into fluid flow communication with the flow path of the injection site.

Repetitive punctures of the septum with a cannula or a needle leads to "coring" or damage to the septum. This in turn leads to a potential source of contamination from the environment, and may also lead to leaking through the damaged portion of the septum.

Pointed cannulae and needles also present a potential hazard to medical personnel. Due to problems associated with infectious blood-borne agents such as the AIDS virus, personnel using such pointed cannulae do so with great care. Notwithstanding careful and prudent practice it is possible for medical personnel to puncture their skin with a pointed cannula which could possibly lead to infection of that person.

As set forth in commonly assigned U.S. Pat. Nos. 5,158,554; 5,167,648; 5,171,234; and 5,188,620, these problems of coring and skin puncturing have lead to the development of cannula embodiments with blunt ends that do not puncture the skin of medical personnel. These blunt cannulae are used with injection sites having pre-slit septums.

While blunt cannulas can pierce pre-slit septums, they are ineffective in piercing solid rubber stoppers. This is significant as drug vials are typically sealed with such solid stoppers.

In an effort to overcome some of these difficulties, devices known as "dispensing pins" can be used to penetrate the stopper of drug vials. Such dispensing pins are typically a sharp spike cannula and can employ a check valve in an effort to prevent gross fluid leakage. On the opposing end of the cannula is a standard luer fitment typically closed off, when not in use, by a cap. These dispensing pins tend to disengage from the vial stopper so that some leakage may occur.

Disclosed in U.S. Pat. No. 5,100,394; a pre-slit injection site assembly has an injection site and a piercing point for coupling the site to a standard drug vial. Primarily developed for use with multi-dose vials, such an assembly can be lockingly engaged with a drug vial, thereby permitting the usage of a blunt cannula rather than a sharp cannula or needle. However, this assembly may not be a cost efficient device when used with single-dose drug vials.

SUMMARY OF THE INVENTION

In accordance with the present invention, a piercing member is adapted to be used with a cannula assembly so that the cannula may pierce a rubber septum of a drug vial or other type of unslit closure. The cannula assembly includes a blunt cannula which may be of one of the several designs previously disclosed in the patents identified above, and a piercing member which can be held by or contained within the flow channel of, the cannula.

Generally, the piercing member includes a tip having a penetrating member of various shapes and designs including a sharpened or spike point capable of piercing an unslit stopper or closure. The piercing member further includes a shaft extending from the tip and a means to release the piercing member from the cannula while preventing inadvertent disengagement of the piercing member from the cannula. Attached to a receiver, such as a standard syringe, the cannula assembly is inserted through the vial stopper and into the vial so that the vial fluid can be infused into the receiver. After infusion, the cannula assembly is withdrawn from the vial with the piercing member being contained within and disposed with the vial. Used in this manner, the cannula assembly allows the medical professional to access a standard drug vial with minimal exposure to a sharpened piercing member and is left with a blunt cannula to conclude the drug administration procedure to a patient.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIGS. 3A, 3B and 3C are cross-sectional views illustrating the operation of the cannula assembly;

FIGS. 4, 5 and 6 are perspective views of alternative embodiments of the piercing member;

DETAILED DESCRIPTION OF A PREFERRED EMBODIMENTS

Figure 1:
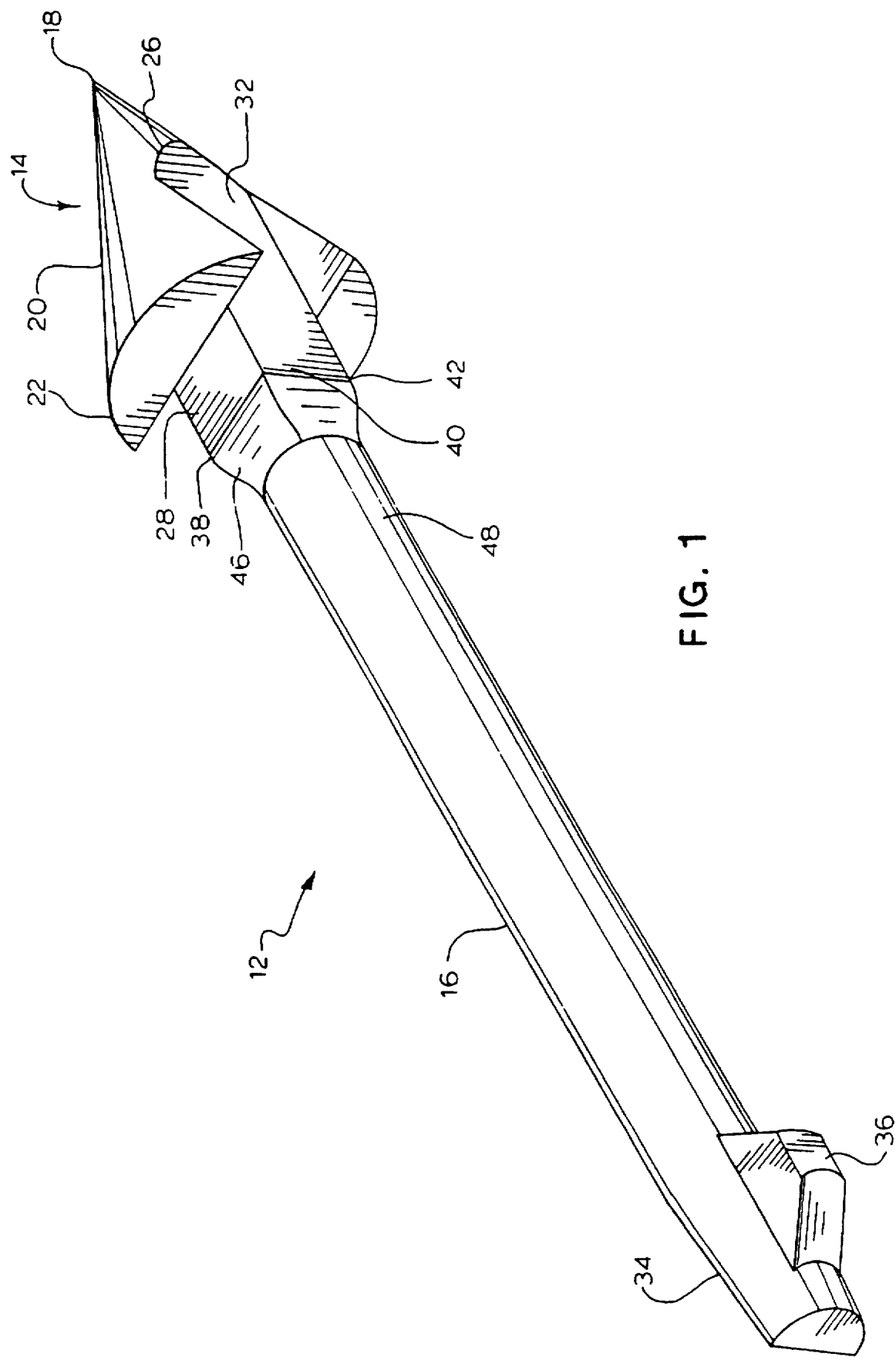
FIG. 1 is a perspective view of the preferred piercing member.
Figure 2:
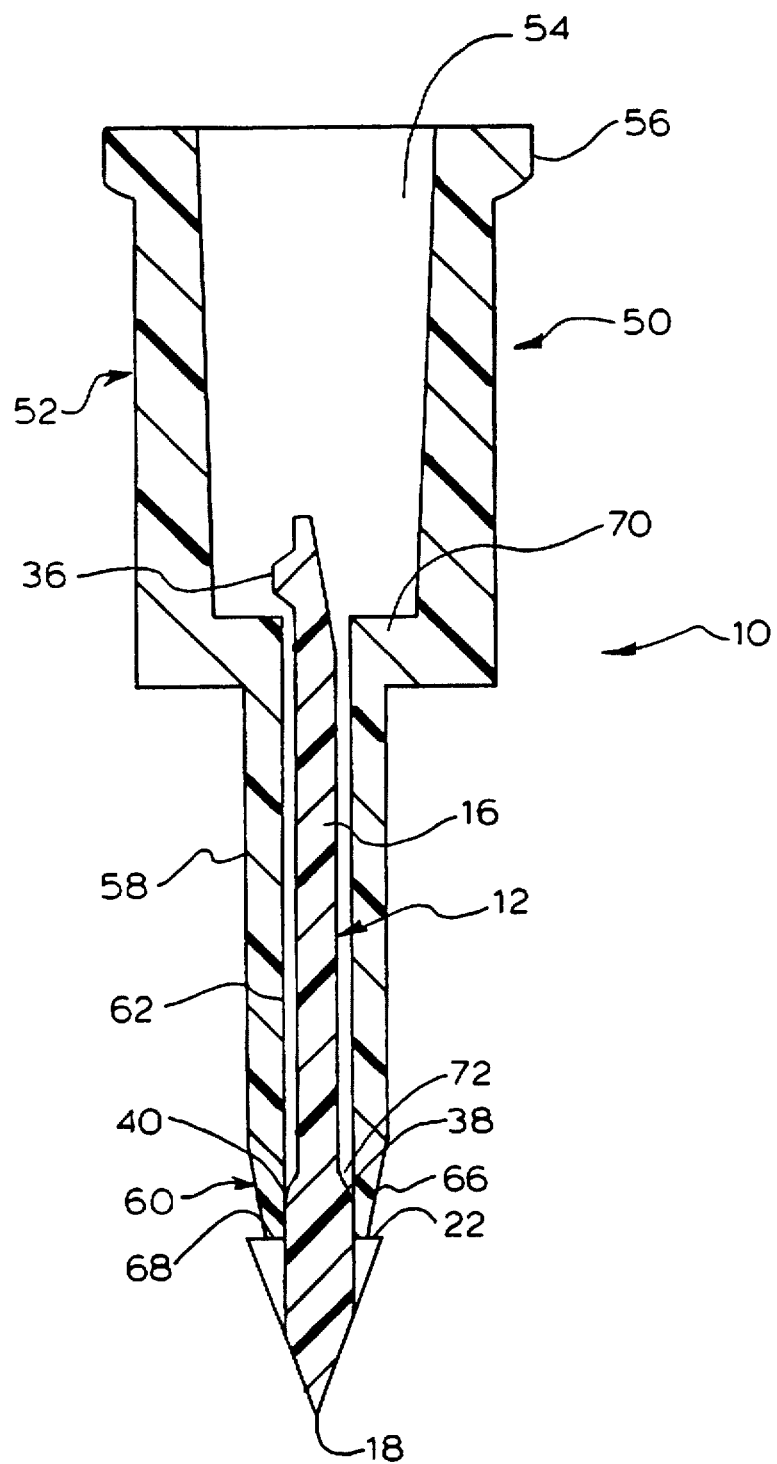
FIG. 2 is a cross-sectional view of the preferred piercing member as contained in the cannula assembly.

The preferred embodiment of the piercing member 12 of the present invention is illustrated in FIG. 1 and as part of the cannula assembly 10 of the present invention, in FIG. 2. The piercing member 12 includes a tip 14, a shaft 16 and a retention means. Preferably of a general conical shape, tip 14 has a penetrating member that is a sharpened or spike point 18, a body portion 20 and a base 22. Body portion 20 is provided with at least one cutout, preferably two cutouts 24 and 26. The shaft 16 has a squared off portion 28 fitting within cutouts 24, 26 so that shaft 16 is integrally connected with and extending from tip 14. At least one channel, preferably two channels 30 and 32, are created by the fitment of squared portion 28 and cutouts 24, 26. The shaft 16 terminates at the opposing end in a taper surface 34. Opposing taper surface 34, retention means in the preferred embodiment includes a generally trapezoidal shaped protuberance 36.

The preferred embodiment shown in FIG. 1 also includes an alignment means which is a series of corners 38, 40, 42 and 44 positioned at the termination of squared portion 28. From corners 38, 40, 42 and 44 the shaft conforms or transits in region 46 from the generally squared portion 28 into a generally cylindrical extension 48.

The cannula assembly 10 illustrated in FIG. 2, includes a blunt cannula 50 and piercing member 12. As described in pending applications, the cannula 50 includes a proximal end 52 defining an interior region 54 and may have a luer flange 56 for connection to a suitable mating engaging structure such as a syringe. A generally cylindrical mid-region 58 extends from the proximal end 52 and an end region 60 extends from the mid-region 58. This embodiment of the cannula 50 minimizes kick-back or recoil owing to the provisions of substantially cylindrical mid-region 58. This embodiment of the cannula 50 also increases withdrawal or tug resistance.

A generally cylindrical internal flow channel 62 extends through the end region 60 and mid-region 58 in communication with the interior region 54 of the proximal end region 52. The end region 60 is provided with a tapered surface 66 to minimize the insertion force.

The shaft 16 of piercing member 12 is slidably received within flow channel 62 of blunt cannula 50 through end region 60. When completely received within cannula 50, shaft 16 extends into interior region 54 of cannula 50 and base 22 contacts the distal blunt end 68 of end region 60. In this embodiment, the protuberance 36 is positioned against the stepped wall 70 between proximal end 52 and mid-region 58 to prevent the inadvertent disengagement of piercing member 12 and cannula 50. Corners 38, 40, 42 and 44 align or center piercing member 12 within flow channel 62. Since the outer diameter of shaft 16 is slightly less than the interior diameter of flow channel 62, a void 72 is created between shaft 16 and interior surfaces of end region 60 and mid-region 58. Void 72 permits fluid and air flow through flow channel 62 despite the presence of shaft 16.

This embodiment of cannula assembly 10 can be packaged as a single-use medical device in a sterile blister pack and utilize a standard tip protector cover over cannula assembly 10. As best illustrated in FIGS. 3A–3C, cannula assembly 10 is removed from the blister pack and releasably connected to a fluid flow member or receiver such as a syringe 74 of known construction. Following drug package instructions, a standard single use drug vial 76 having a solid closure or stopper 78 is prepared. After removal of the tip protector, a volume of air can be drawn into or expelled from syringe 74, if required, without dislodging cannula assembly 10. The cannula assembly 10 connected with syringe 74 is then positioned at the center of stopper 78 and pressed firmly towards vial 76 so that piercing member 12 pierces through stopper 78. To reduce the insertion force required, tip 14 can be lubricated, for example, during the manufacturing process, with silicone.

As shown in FIG. 3B, cannula assembly 10 is inserted through stopper 78 until stepped wall 70 provides a positive stop to insertion by meeting the upper surface of either vial 76 and/or stopper 78. Complete insertion is achieved when tip 14 and the immediate portion of shaft 16 pass beyond stopper 78 and enter the vial chamber 80. In this example, the liquid held in vial chamber 80 can now be removed through cannula assembly 10 and into the syringe 74. Once the liquid has been removed from chamber 80, syringe 74 and cannula assembly 10 are withdrawn from vial 76. As cannula assembly 10 exits stopper 78, base 22 of tip 14 meets stopper 78 and prohibits the further withdrawal of piercing member 12. At this point of the withdrawal procedure, sufficient force is created to cause taper surface 34 to deflect, permitting protuberance 36 to slide over stepped wall 70 and through flow channel 62, thereby permitting the disengagement of piercing member 12 from cannula 50.

As illustrated in FIG. 3C, cannula 50 while still connected with syringe 74, is completely withdrawn from stopper 78. Piercing member 12 remains either in the vial chamber 80 or imbedded in stopper 78. The vial 76 with piercing member 12 can then be disposed of without the user having any further exposure to spike point 18 or piercing member 12. The syringe 74 with cannula 50 is now ready for insertion into an injection site or other closure having a pre-slit septum, for example, as those disclosed in related pending applications.

Figure 10:
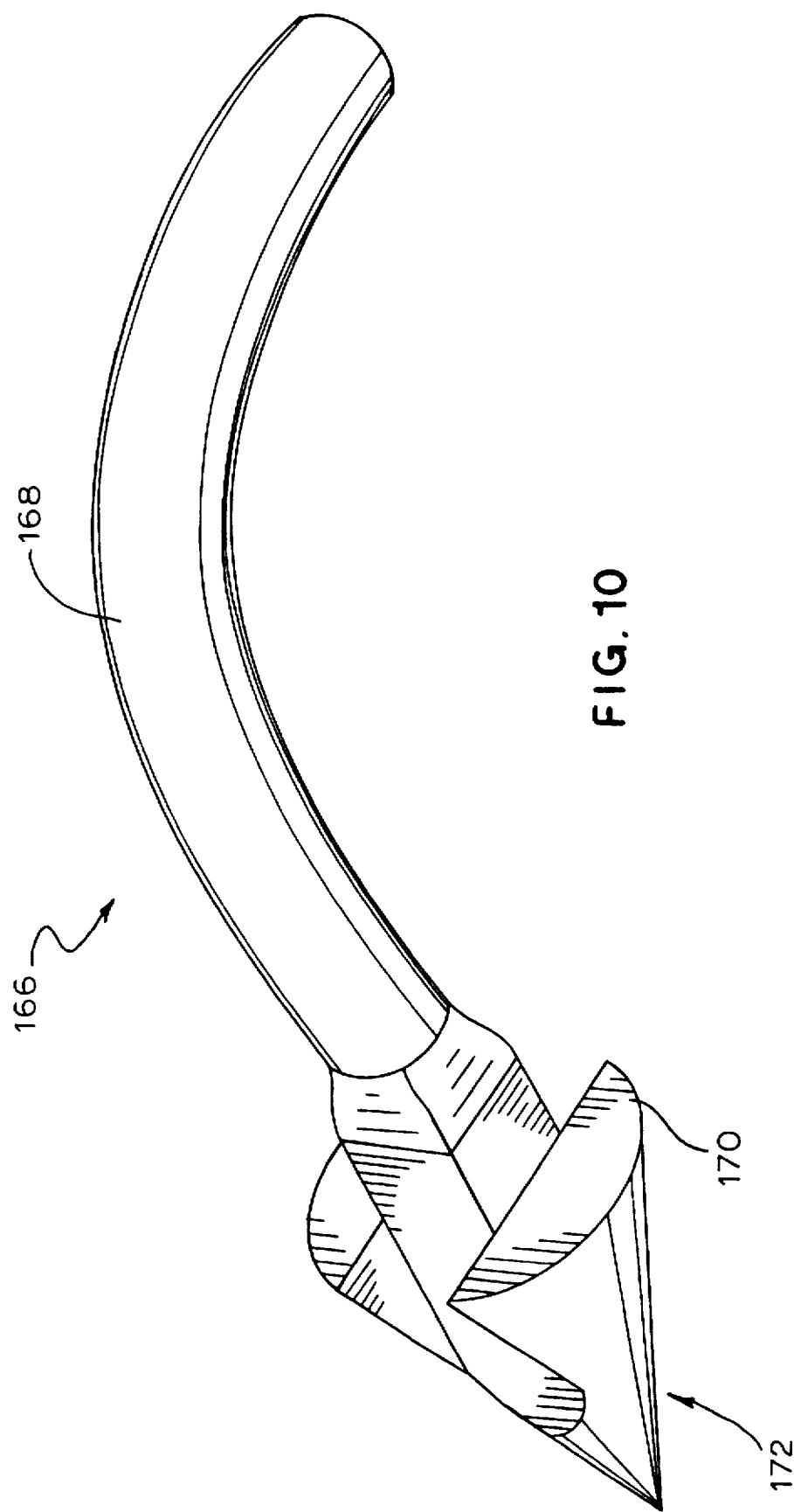
FIGS. 10, 11 and 12 are perspective views of alternative embodiments of the piercing member.

Although the retention means of the preferred embodiment of the cannula assembly 10 has been described as a force fit between protuberance 36 and stepped wall 70, retention could be achieved when protuberance 36 remains in flow channel 62 of mid-region 58 causing the end of shaft 16 to flex and contact at least some portion of the inner surface or wall of mid-region 58. Retention could also be achieved through a spring-type action. Absent protuberance 36, a spring action retention means can be achieved through a naturally arced or curved shaft 168 as shown in FIG. 10. The curved shaft 168 has sufficient flexibility so that the shaft 168 generally straightens upon insertion into flow channel of the cannula. When the base 170 of tip 172 contacts the vial stopper and causes the separation of the piercing member 166 from the cannula, the shaft 168 returns to its natural curved state.

Further variations on piercing member are illustrated in FIGS. 4–6 and 12 with the following description highlighting some of the distinctions between the embodiments. Shown in FIG. 4, piercing member 90 includes a solid tip 92 with a pair of stand-offs 94 and 96 positioned on the base 98 of tip 92. Upon assembly of cannula 50 and piercing member 90, stand-offs 94, 96 rest against distal blunt end 68 of cannula 50. Stand-offs 94, 96 create a void 100 to permit fluid and air flow through the flow channel 62 of cannula 50. In addition, piercing member 90 is provided with a retention means including a generally semi-circular shaped protuberance 102 differing from the preferred protuberance 36 in shape. Protuberance 102 cooperates with a stepped portion 104 of the terminal end of shaft 106 in the appropriate retention through either force fit or a spring action, of piercing member 90 within cannula 50.

Figure 5:
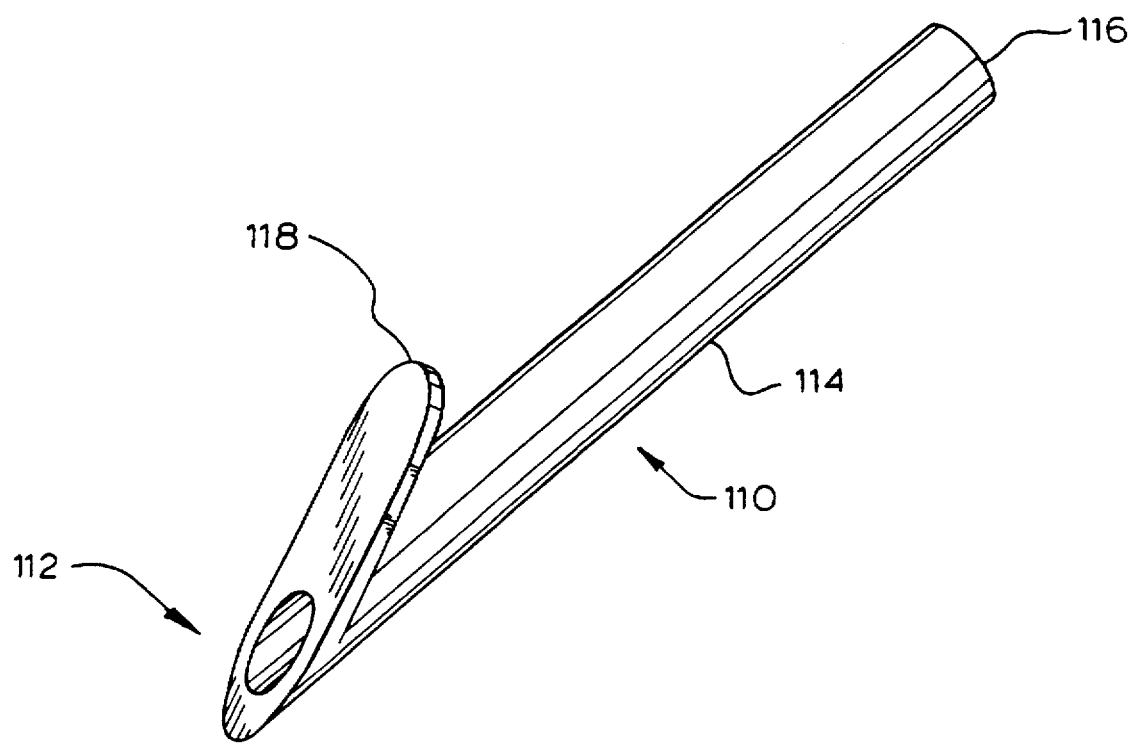

FIG. 5 illustrates a third embodiment of piercing member 110. A hollow bore 113 extends through the piercing member 110 from the generally v-shaped tip 112 to the terminal end 116 of the shaft 114. Although the shaft 114 is generally cylindrical in shape, it has an outer diameter which gradually decreases from the integral connection with tip 112 to the terminal end 116 of shaft 114. In this manner, piercing member 110 is force fit into flow channel 62 of cannula 50. The piercing member 110 will remain either in the vial chamber 80 or imbedded in stopper 78 upon withdrawal of cannula 50 as the base 118 of the v-shaped tip 112 does not permit withdrawal from stopper 78.

As can be appreciated, the force fit of piercing member 110 can also be achieved by reversing the variation of the outer diameter, that is increasing from integral connection with tip 112 to terminal end 116 of shaft 114. The force fit retention is achieved as long as interference occurs at some point along the shaft and the inner surface of cannula.

Figure 6:
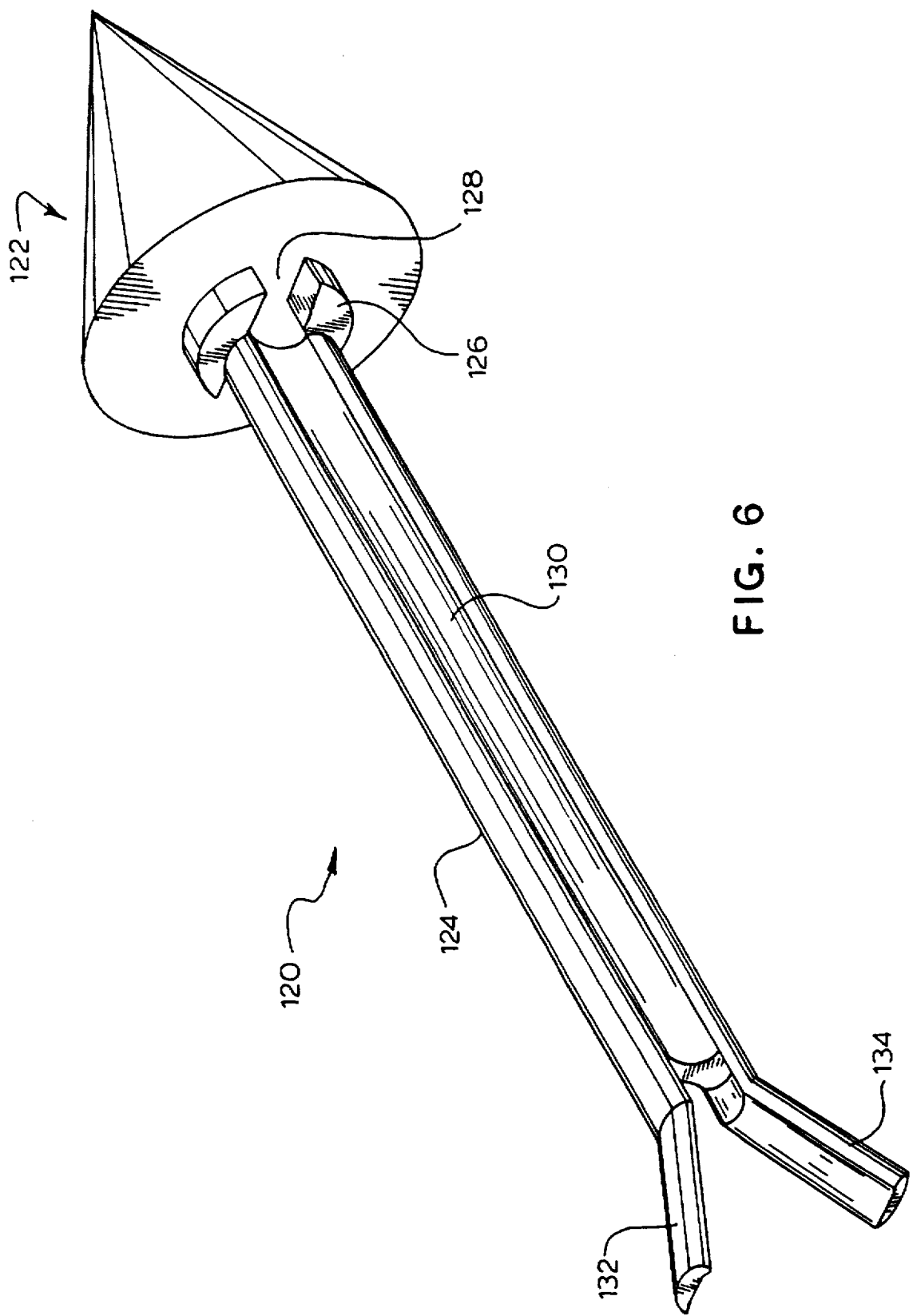

FIG. 6 also illustrates another embodiment of piercing member 120 differing in a solid tip 122 integrally connected with the shaft 124 at a thickened neck portion 126 of shaft 124. The neck portion 126 is of a sufficient thickness so as to provide a void 128 between distal blunt end 68 and tip 122. Running longitudinally through shaft 124, a groove 130 is formed to permit fluid flow along shaft 124. Rather than terminally end with a taper surface and protuberance, the piercing member 120 is provided with a pair of deflecting fingers 132, 134 which can be forcibly flexed inward or toward one another upon assembly of piercing member 120 and cannula 50. Upon insertion in flow channel 62, deflecting fingers 132, 134 will naturally flex outwardly once they pass stepped wall 70 of cannula 50, thereby functioning similarly to tapered surface 34 and protuberance 36. Further, if deflecting fingers 132, 134 do not pass stepped wall 70, but remain in flow channel 62, deflecting fingers 132, 134 will achieve retention of piercing member 120 in cannula 50 through a spring action.

Figure 7:
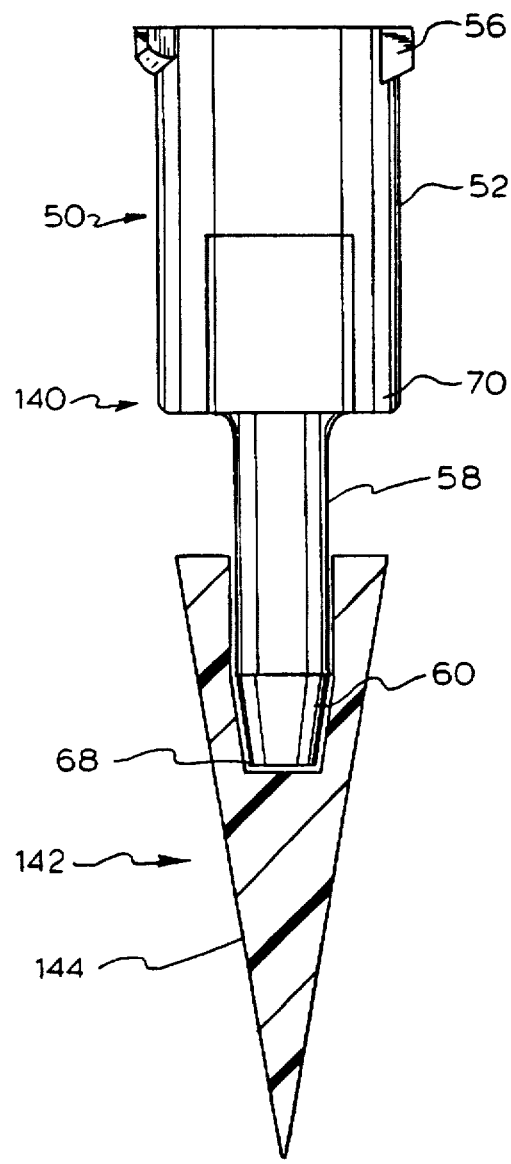
FIGS. 7, 8 and 9 are cross-sectional views of alternative embodiments of the cannula assembly.
Figure 9:
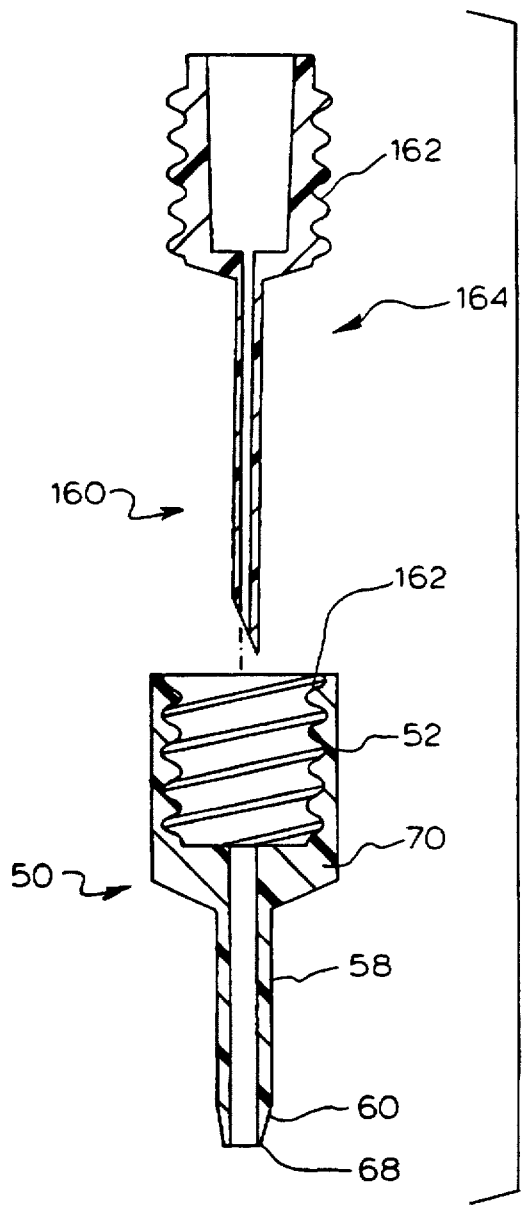
Figure 8:
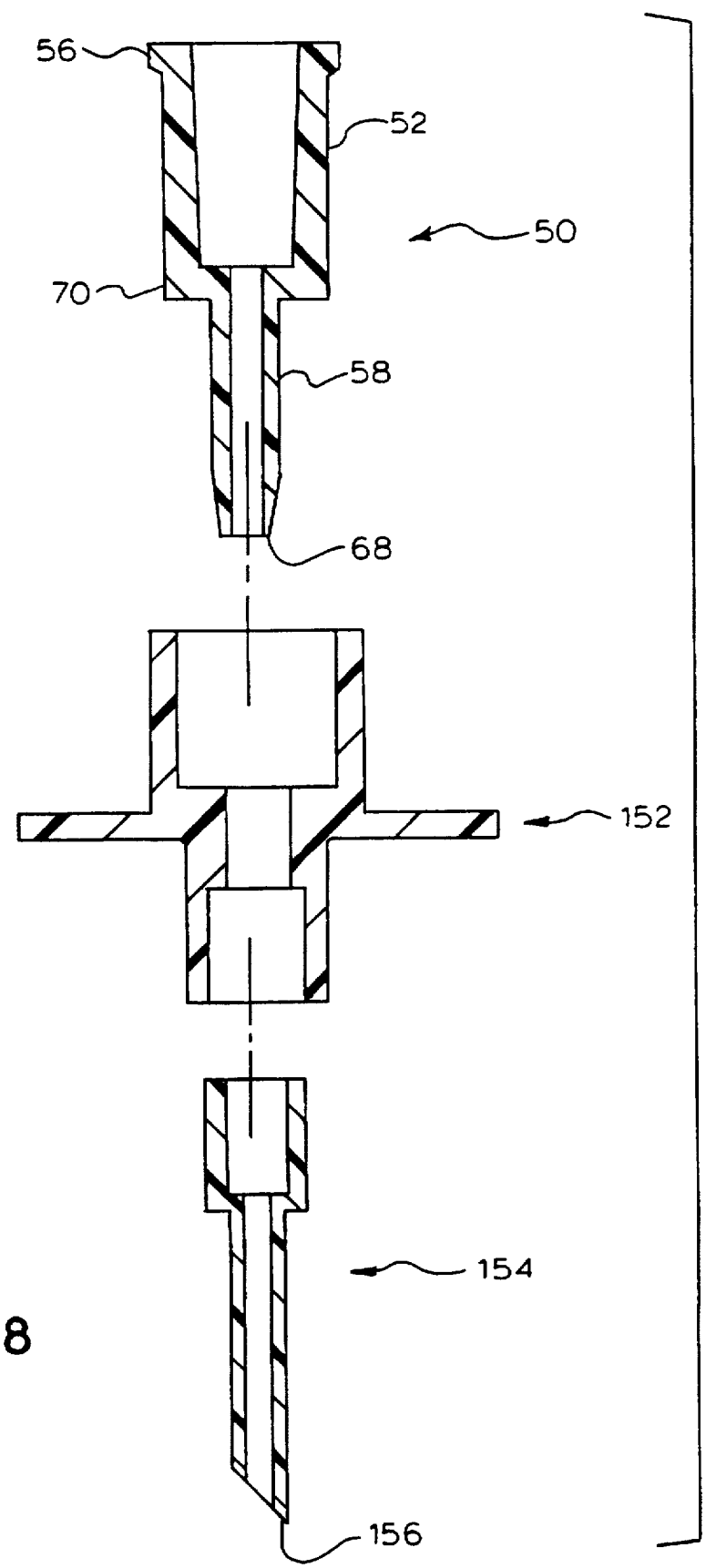

Additional embodiments of the cannula assembly are illustrated in FIGS. 7, 8 and 9. The cannula assembly 140 shown in FIG. 7 includes a piercing member 142 having a tip 144 of an arrowhead shape which is friction fit over distal blunt end 68 of cannula 50 as opposed to a force fit or spring action retention within the flow channel of the cannula. Upon insertion and withdrawal of assembly 140, piercing member 142 parts from cannula 50 and remains in the drug vial chamber 80.

FIGS. 8 and 9 illustrate cannula assemblies 150 and 160 which utilize a positive connecting means such as a flexible coupling member 152 in FIG. 8 or a threaded lock 162 as in FIG. 9, to permit appropriate retention and separation between piercing members 154 or 164 and cannula 50. The cannula assembly 150 illustrated in FIG. 8 further provides an assembly which permanently incorporates the piercing member 154 inside of the cannula 50 and prohibits the piercing member 154 from becoming imbedded in the vial stopper 78 upon withdrawal of the assembly 150. Rather, the piercing member 154 is retracted within the cannula 50 through a twist motion so that the spike point 156 of the piercing member 154 is retracted into and contained within flow channel 62 of cannula 50. After administration of the fluid from the syringe, the entire cannula assembly 150 can then be disposed of without the user coming in contact with the spike point 156 of the piercing member 154.

Figure 11:
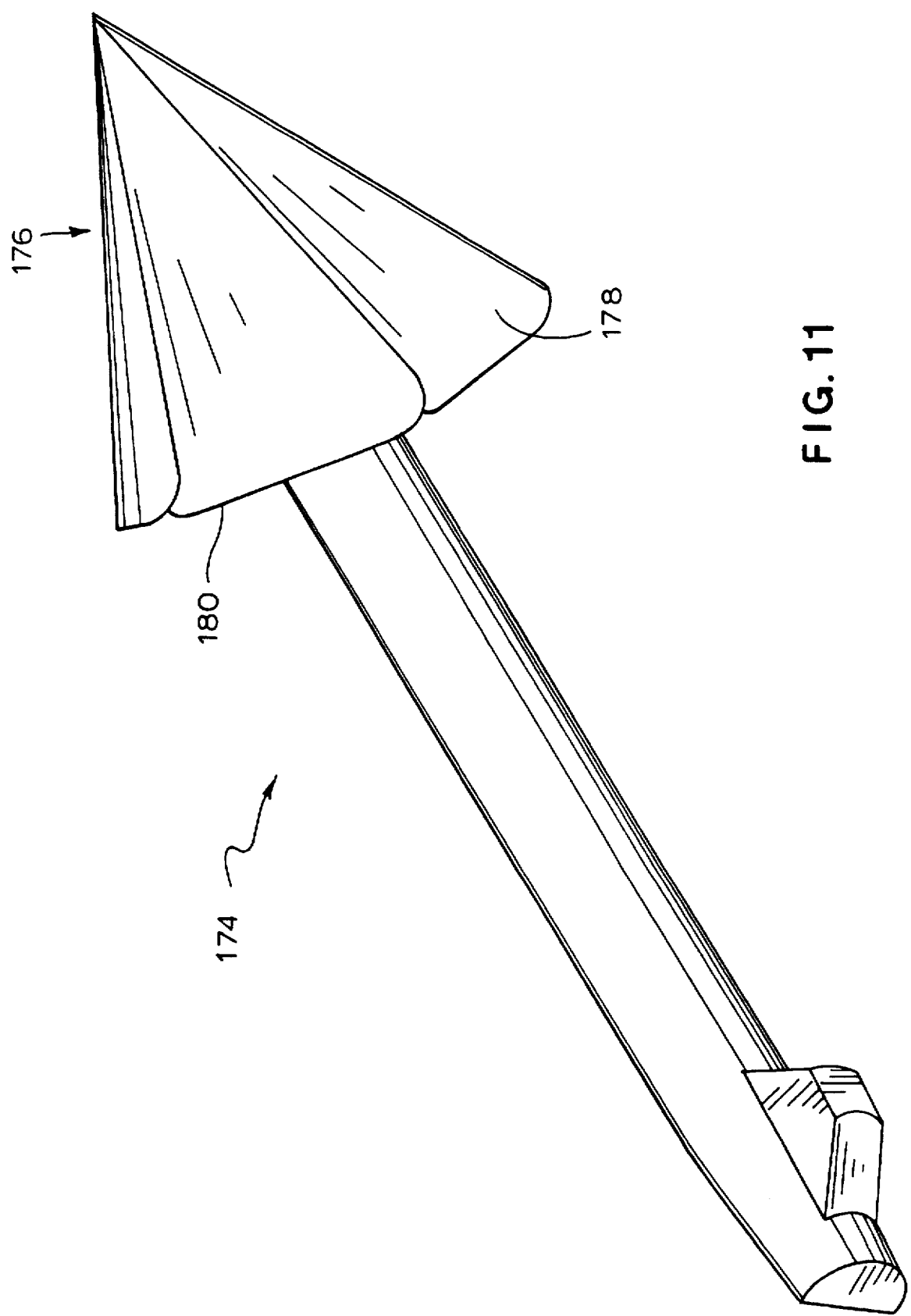
Figure 12:
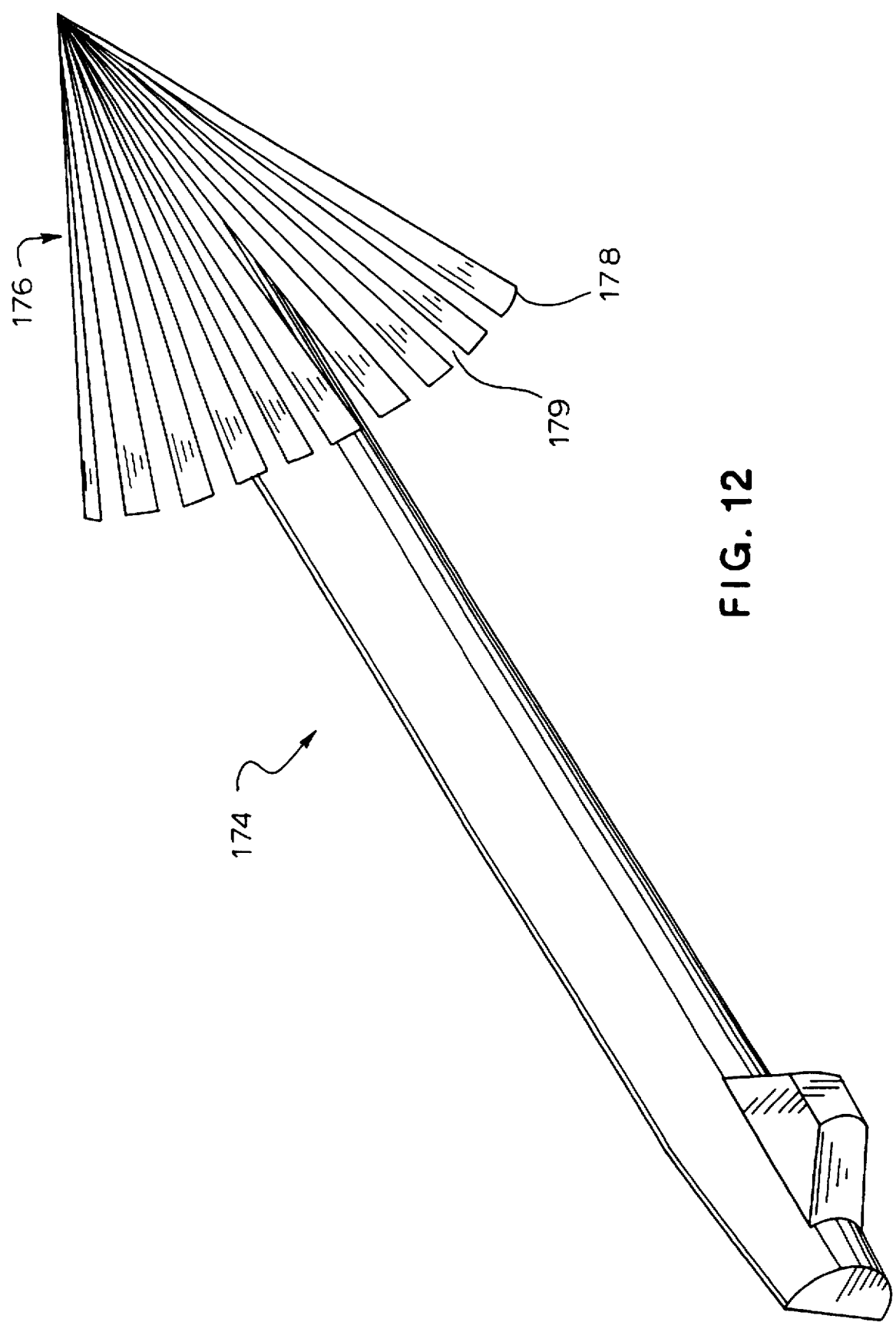

FIGS. 11 and 12 show a piercing member 174 having a tip 176 with a plurality of flexible fingers 178, creating an umbrella-like structure, as shown in FIG. 11. FIG. 12 shows another embodiment of the umbrella-like structure having a plurality of gaps 179 separating the fingers 178. Any number of fingers 178 and gaps 179 may be used without departing from the invention as long as they function as described below.

Upon insertion of these cannula assemblies into a drug vial stopper, the flexible fingers 178 will fold in or close. This allows the diameter at the base 180 of the tip 176 to be significantly greater than the diameter of the cannula. After complete insertion, the flexible fingers 178 will relax in a partially opened state. Upon withdrawal of such an assembly, the flexible fingers 178 will contact the underside of the stopper and fan out, causing the separation of the piercing member 174 from the cannula. An advantage of this embodiment is to prevent the inadvertent withdrawal of the piercing member 174 from the vial.

From the description of these various embodiments, it is clear that numerous modifications to the cannula assembly come to mind without significantly departing from the spirit of the invention, and the scope of protection is only limited by the scope of the accompanying claims.

We claim:

1. A piercing member adapted for use with a flow channel for piercing a solid closure or stopper comprising:

means associated with the piercing member for retaining the piercing member to the flow channel;

means associated with the piercing member adapted for allowing fluid to flow through the flow channel when the piercing member is retained to the flow channel; and a tip on the piercing member having a penetrating member at a distal end of the tip, the flow means comprising cutouts in the penetrating member of the tip.

2. The piercing member of claim 1 wherein the piercing member includes a shaft and wherein the retaining means comprises a protuberance on the shaft.

3. The piercing member of claim 2 wherein the protuberance is on an end of the shaft opposite the tip.

4. The piercing member of claim 2 wherein the protuberance is generally trapezoidal shaped.

5. The piercing member of claim 2 wherein the protuberance is generally semi-circular in shape.

6. The piercing member of claim 2 wherein the shaft comprises a generally square elongate extension.

7. The piercing member of claim 1 wherein the retaining means comprises a shaft attached to the tip and having a dimension that is adapted to form an interference fit with the flow channel.

8. The piercing member of claim 1 wherein the penetrating member is generally conically shaped.

9. The piercing member of claim 1 wherein the penetrating member is a generally arrowhead structure.

10. The piercing member of claim 1 wherein the penetrating member is a generally umbrella structure.

11. The piercing member of claim 1 further including a generally curved cylindrical shaped shaft extending from the tip wherein said retaining means comprises a friction fit between the shaft and the flow channel of the cannula assembly.

12. The piercing member of claim 1 wherein the penetrating member is generally v-shaped.

13. The piercing member of claim 1 wherein the piercing member further includes means for retaining the piercing member to the stopper.

14. A piercing member adapted for use with a flow channel for piercing a solid closure or stopper comprising:

means associated with the piercing member for retaining the piercing member to the flow channel;

means associated with the piercing member adapted for allowing fluid to flow through the flow channel when the piercing member is retained to the flow channel; and a penetrating member having a distal tip and disposed at an end of the piercing member, the penetrating member has a base extending away from the tip and the flow means comprises cutouts in the base of the penetrating member.

15. A piercing member adapted for use with a flow channel for piercing a solid closure or stopper comprising:

means associated with the piercing member for retaining the piercing member to the flow channel;

means associated with the piercing member adapted for allowing fluid to flow through the flow channel when the piercing member is retained to the flow channel; and a tip on the piercing member having a penetrating member at a distal end of the tip, the piercing member has a base and a shaft, the shaft extending away from the base, the flow means comprising a fluid channel extending through the shaft.

16. The piercing member of claim 15 wherein the shaft is generally cylindrically shaped.

17. The piercing member of claim 15 wherein the shaft is generally cylindrically shaped and having a portion removed to define a longitudinal groove.

18. A piercing member adapted for use with a flow channel for piercing a solid closure or stopper comprising:

means associated with the piercing member for retaining the piercing member to the flow channel;

means associated with the piercing member adapted for allowing fluid to flow through the flow channel when the piercing member is retained to the flow channel; and a tip on the piercing member having a penetrating member at a distal end of the tip, the piercing member includes a shaft attached to the tip, and wherein the retaining means comprises a pair of opposed fingers at a proximal end of the shaft.

19. A piercing member adapted for use with a flow channel for piercing a solid closure or stopper comprising:

means for retaining the piercing member to the flow channel;

means for allowing fluid to flow through the flow channel; and a tip comprising:

a penetrating member at a distal end of the tip;

a body; and a plurality of extensions integral with the penetrating member wherein the extensions fold into the tip when the cannula assembly is inserted into the stopper and the extensions open when the cannula assembly is being withdrawn, thereby causing release of the retaining means when the cannula assembly is withdrawn from the stopper.

20. A piercing member adapted for use with a flow channel for piercing a solid closure or stopper comprising:

means for retaining the piercing member to the flow channel;

means for allowing fluid to flow through the flow channel when the piercing member is retained to the flow channel;

a shaft having a tip at a distal end of the shaft; and, means associated with the shaft for aligning the piercing member with the flow channel, the piercing member having a portion removed to define a cutout to provide a flow path to the flow channel.

21. The piercing member of claim 20 wherein the means for aligning the piercing member with the shaft includes a plurality of corners on the shaft.

22. A piercing member adapted for use with a blunt cannula forming a flow channel, the piercing member comprising:

a shaft having distal and proximal ends and adapted to fit within the flow channel;

a penetrating member at the distal end of the shaft and having a portion removed to define a cutout to provide fluid communication with the flow channel; and, a protuberance at the proximal end of the shaft to contact the cannula and removable retain the shaft.

23. The piercing member of claim 22 wherein the penetrating member has two cutouts.

24. The piercing member of claim 22 wherein the shaft has a generally square shaped cross section proximate the tip.

25. The piercing member of claim 24 wherein the standoffs extend in generally the same direction as the shaft.

26. The piercing member of claim 22 wherein the proximal end has a portion that tapers inwardly.

27. The piercing member of claim 22 wherein the protuberance is generally trapezoidal in shape.

28. The piercing member of claim 22 wherein the protuberance is generally semi-circular in shape.

29. A piercing member adapted for use with a cannula for piercing a solid closure comprising:

a forward tip with a pointed end and a base, a plurality of standoffs extending from the base and contacting the cannula to form flow voids and provide fluid communication with the flow channel of the cannula; and a rearward extending shaft extending within a flow channel defined by the cannula, the shaft and cannula being sized to allow fluid flow through the flow channel when the shaft is disposed within the channel.

30. A piercing member adapted for use with a cannula for piercing a solid closure comprising:

a forward tip with a pointed end and a base, the forward tip forming a plurality of standoffs extending from the base and contacting the cannula to space the base from the cannula and form flow voids and provide fluid communication with the flow channel of the cannula; and a rearward extending shaft extending within a flow channel defined by the cannula, the shaft and cannula being sized to allow fluid flow through the flow channel when the shaft is disposed within the channel.

* * * * *